(12) United States Patent
Cane'

(10) Patent No.: US 7,407,493 B2
(45) Date of Patent: Aug. 5, 2008

(54) CONTAINER FOR DISPOSABLE NEEDLE OR CANNULA

(75) Inventor: Mario Cane', Collegno (IT)

(73) Assignee: Unomedical A/S, Birkeroed (DK)

( * ) Notice: Subject to any disclaimer, the term of this patent is extended or adjusted under 35 U.S.C. 154(b) by 343 days.

(21) Appl. No.: 10/872,423

(22) Filed: Jun. 22, 2004

(65) Prior Publication Data

US 2005/0035014 A1    Feb. 17, 2005

(51) Int. Cl.
*A61M 37/00*  (2006.01)
*A61M 5/178*  (2006.01)

(52) U.S. Cl. .................. 604/181; 604/131; 604/156; 206/365

(58) Field of Classification Search .................. 206/365; 604/180, 131, 171, 163, 156, 164.01, 136, 604/192, 198, 135, 181; 606/167, 184, 185
See application file for complete search history.

(56) References Cited

U.S. PATENT DOCUMENTS

| | | | |
|---|---|---|---|
| 2,047,010 A | 7/1936 | Dickinson | |
| 2,295,849 A | 9/1942 | Kayden | |
| 2,690,529 A | 9/1954 | Lindblad | |
| 2,936,141 A | 5/1960 | Rapata | |
| 3,074,541 A | 1/1963 | Roehr | |
| 3,545,286 A | 12/1970 | Stenstrom | |
| 3,547,119 A | 12/1970 | Hall et al. | |
| 3,610,240 A | 10/1971 | Harautuneian | |
| 3,810,469 A * | 5/1974 | Hurschman | 604/88 |
| 3,840,011 A | 10/1974 | Wright | |
| 3,937,219 A | 2/1976 | Karakashian | |
| 3,986,508 A | 10/1976 | Barrington | |
| 4,022,205 A | 5/1977 | Tenczar | |
| 4,188,950 A | 2/1980 | Wardlaw | |
| 4,201,406 A | 5/1980 | Dennehey et al. | |
| 4,227,528 A | 10/1980 | Wardlaw | |
| 4,267,836 A | 5/1981 | Whitney et al. | |
| 4,315,505 A | 2/1982 | Crandall et al. | |

(Continued)

FOREIGN PATENT DOCUMENTS

DE    196 31 921 A1    3/1997

(Continued)

*Primary Examiner*—Mickey Yu
*Assistant Examiner*—Steven A. Reynolds
(74) *Attorney, Agent, or Firm*—Brinks Hofer Gilson & Lione (57) ABSTRACT

The present invention relates to a container for a disposable needle or cannula, intended to facilitate needle or cannula placement for the infusion of a liquid drug under a patient's skin, the container including a cylindrical housing (1; 101) in which there are defined a cap (1a; 101a) and a sleeve (1b; 101b) provided with a resting base (1c; 101c), the cap (1a; 101a) being axially slidable relative to the sleeve (1b; 101b) when a sufficient pressure is exerted on the cap (1a; 101a); a needle (21; 121) or cannula, which is located inside the housing so as to be directed towards the resting base (1c; 101c) for the infusion of the drug; a retaining member (9; 109), which is located within the housing (1; 101) between said cap (1a; 101a) and the sleeve (1b; 101b) and to which the needle (21; 121) or cannula is secured; the container being equipped with a releasing member for releasing the needle (21; 121) or cannula when the cap (1a; 101a) is made to slide on the sleeve (1b; 101b).

35 Claims, 8 Drawing Sheets

U.S. PATENT DOCUMENTS

| | | |
|---|---|---|
| 4,333,455 A | 6/1982 | Bodicky |
| 4,334,551 A | 6/1982 | Pfister |
| D267,199 S | 12/1982 | Koenig |
| 4,417,886 A | 11/1983 | Frankhouser et al. |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,563,177 A | 1/1986 | Kamen |
| 4,610,469 A | 9/1986 | Wolff-Mooij |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,878,897 A | 11/1989 | Katzin |
| 4,890,608 A | 1/1990 | Steer |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,248,301 A | 9/1993 | Koenig et al. |
| 5,256,152 A | 10/1993 | Marks |
| 5,257,980 A | 11/1993 | Van Antwerp et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A * | 2/1995 | Wilmot ..................... 604/139 |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,451,210 A | 9/1995 | Kramer et al. |
| 5,487,506 A | 1/1996 | Drummond et al. |
| 5,490,841 A | 2/1996 | Landis |
| 5,492,313 A | 2/1996 | Pan et al. |
| 5,501,675 A | 3/1996 | Erskine |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A | 6/1996 | Teissen-Simony |
| 5,527,287 A * | 6/1996 | Miskinyar ................... 604/135 |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,700,250 A | 12/1997 | Erskine |
| 5,704,920 A | 1/1998 | Gyure |
| 5,709,516 A | 1/1998 | Peterson et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| D402,538 S | 12/1998 | Wagter et al. |
| 5,843,001 A | 12/1998 | Goldenberg |
| 5,848,990 A | 12/1998 | Cirelli et al. |
| 5,851,197 A * | 12/1998 | Marano et al. ............. 604/135 |
| 5,858,001 A | 1/1999 | Tsals et al. |
| 5,865,806 A | 2/1999 | Howell |
| 5,873,540 A | 2/1999 | Hardin |

| | | | | | | |
|---|---|---|---|---|---|---|
| 5,899,886 A | 5/1999 | Cosme | | 6,607,509 B2 | 8/2003 | Bobroff et al. |
| 5,911,705 A | 6/1999 | Howell | | 6,607,511 B2 | 8/2003 | Halseth |
| 5,913,846 A | 6/1999 | Szabo | | 6,613,064 B2 | 9/2003 | Rutynowski et al. |
| 5,915,640 A | 6/1999 | Wagter et al. | | 6,620,136 B1 | 9/2003 | Pressly, Sr. et al. |
| 5,916,199 A | 6/1999 | Miles | | 6,629,949 B1 | 10/2003 | Douglas |
| 5,919,167 A | 7/1999 | Mulhauser et al. | | 6,645,182 B1 | 11/2003 | Szabo |
| 5,925,032 A | 7/1999 | Clements | | 6,659,982 B2 | 12/2003 | Douglas et al. |
| 5,947,931 A | 9/1999 | Bierman | | 6,685,674 B2 | 2/2004 | Douglas et al. |
| 5,947,935 A | 9/1999 | Rhinehart et al. | | 6,699,218 B2 | 3/2004 | Flaherty et al. |
| 5,951,523 A | 9/1999 | Osterlind et al. | | 6,702,779 B2 | 3/2004 | Connelly et al. |
| 5,954,643 A | 9/1999 | VanAntwerp et al. | | 6,726,649 B2 | 4/2004 | Swenson et al. |
| 5,957,892 A | 9/1999 | Thorne | | 6,736,797 B1 | 5/2004 | Larsen et al. |
| 5,968,011 A | 10/1999 | Larsen et al. | | 6,749,589 B1 | 6/2004 | Douglas et al. |
| 5,975,120 A | 11/1999 | Novosel | | 6,790,199 B1 | 9/2004 | Gianakos |
| 5,980,488 A | 11/1999 | Thorne | | 6,805,686 B1 | 10/2004 | Fathallah et al. |
| 5,980,506 A | 11/1999 | Mathiasen | | 6,811,545 B2 | 11/2004 | Vaillancourt |
| 5,984,224 A | 11/1999 | Yang | | 6,814,720 B2 | 11/2004 | Olsen et al. |
| 5,984,897 A | 11/1999 | Petersen et al. | | 6,824,530 B2 | 11/2004 | Wagner et al. |
| 5,992,787 A | 11/1999 | Burke | | 6,824,531 B1 | 11/2004 | Zecha, Jr. et al. |
| D417,733 S | 12/1999 | Howell et al. | | 6,830,562 B2 | 12/2004 | Mogensen et al. |
| 6,017,328 A | 1/2000 | Fischell et al. | | 6,837,877 B2 | 1/2005 | Zurcher |
| D421,119 S | 2/2000 | Musgrave et al. | | 6,837,878 B2 | 1/2005 | Smutney et al. |
| 6,024,727 A | 2/2000 | Thorne et al. | | 6,840,922 B2 | 1/2005 | Nielsen et al. |
| 6,039,629 A | 3/2000 | Mitchell | | 6,880,701 B2 | 4/2005 | Bergeron et al. |
| 6,042,570 A | 3/2000 | Bell et al. | | 6,916,017 B2 | 7/2005 | Noe |
| 6,045,533 A | 4/2000 | Kriesel et al. | | 6,923,791 B2 | 8/2005 | Douglas |
| 6,045,534 A * | 4/2000 | Jacobsen et al. ............ 604/156 | | 6,926,694 B2 | 8/2005 | Marano-Ford et al. |
| 6,050,976 A | 4/2000 | Thorne et al. | | 6,939,331 B2 | 9/2005 | Ohshima |
| 6,056,718 A | 5/2000 | Funderburk et al. | | 6,949,084 B2 | 9/2005 | Marggi et al. |
| 6,056,726 A | 5/2000 | Isaacson | | 6,960,193 B2 | 11/2005 | Rosenberg |
| 6,074,369 A * | 6/2000 | Sage et al. ................ 604/181 | | 6,991,619 B2 | 1/2006 | Marano-Ford et al. |
| 6,074,371 A | 6/2000 | Fischell | | 6,991,620 B2 | 1/2006 | Marano-Ford et al. |
| 6,077,244 A | 6/2000 | Botich et al. | | 6,997,907 B2 | 2/2006 | Safabash et al. |
| 6,086,008 A | 7/2000 | Gray et al. | | 7,018,344 B2 | 3/2006 | Bressler et al. |
| 6,086,575 A | 7/2000 | Mejslov | | 7,022,108 B2 | 4/2006 | Marano-Ford et al. |
| 6,090,068 A * | 7/2000 | Chanut .................... 604/93.01 | | 7,052,483 B2 | 5/2006 | Wojcik |
| 6,093,172 A | 7/2000 | Funderburk et al. | | 7,056,302 B2 | 6/2006 | Douglas |
| 6,093,179 A | 7/2000 | O'Hara et al. | | 2001/0004970 A1 | 6/2001 | Hollister et al. |
| 6,099,503 A | 8/2000 | Stardella | | 2001/0016714 A1 | 8/2001 | Bell et al. |
| 6,105,218 A | 8/2000 | Reekie | | 2001/0021827 A1 | 9/2001 | Ferguson et al. |
| 6,120,482 A | 9/2000 | Szabo | | 2001/0039401 A1 | 11/2001 | Ferguson et al. |
| 6,123,690 A | 9/2000 | Mejslov | | 2001/0041875 A1 | 11/2001 | Higuchi et al. |
| 6,132,755 A | 10/2000 | Eicher et al. | | 2002/0022855 A1 | 2/2002 | Bobroff et al. |
| 6,159,181 A | 12/2000 | Crossman et al. | | 2002/0068904 A1 | 6/2002 | Pluth et al. |
| 6,183,464 B1 | 2/2001 | Sharp et al. | | 2002/0072720 A1 | 6/2002 | Hague et al. |
| 6,191,338 B1 | 2/2001 | Haller | | 2002/0077599 A1 | 6/2002 | Wojcik |
| 6,193,694 B1 | 2/2001 | Bell et al. | | 2002/0082543 A1 | 6/2002 | Park et al. |
| 6,219,574 B1 | 4/2001 | Cormier et al. | | 2002/0107489 A1 | 8/2002 | Lee |
| 6,221,058 B1 | 4/2001 | Kao et al. | | 2002/0111581 A1 | 8/2002 | Sasso |
| 6,248,093 B1 | 6/2001 | Moberg | | 2002/0145073 A1 | 10/2002 | Swanson |
| 6,293,925 B1 | 9/2001 | Safabash et al. | | 2002/0156424 A1 | 10/2002 | Suzuki et al. |
| 6,302,866 B1 | 10/2001 | Marggi | | 2002/0156427 A1 | 10/2002 | Suzuki et al. |
| 6,319,232 B1 | 11/2001 | Kashmer | | 2002/0161332 A1 | 10/2002 | Ramey |
| 6,322,535 B1 | 11/2001 | Hitchins et al. | | 2002/0161386 A1 | 10/2002 | Halseth et al. |
| 6,322,808 B1 | 11/2001 | Trautman et al. | | 2002/0169419 A1 | 11/2002 | Steg |
| 6,334,856 B1 | 1/2002 | Allen et al. | | 2002/0173748 A1 | 11/2002 | McConnell et al. |
| 6,355,021 B1 | 3/2002 | Nielsen et al. | | 2002/0173769 A1 | 11/2002 | Gray et al. |
| 6,379,335 B1 | 4/2002 | Rigon et al. | | 2002/0183688 A1 | 12/2002 | Lastovich et al. |
| D456,692 S | 5/2002 | Epstein | | 2002/0189688 A1 | 12/2002 | Roorda |
| 6,387,076 B1 | 5/2002 | Van Landuyt | | 2002/0193737 A1 | 12/2002 | Popovsky |
| 6,387,078 B1 | 5/2002 | Gillespie, III | | 2002/0193744 A1 | 12/2002 | Alesi et al. |
| 6,405,876 B1 | 6/2002 | Seshimoto et al. | | 2003/0014018 A1 | 1/2003 | Giambattista et al. |
| 6,447,482 B1 * | 9/2002 | Roenborg et al. ............ 604/131 | | 2003/0060781 A1 | 3/2003 | Mogensen et al. |
| 6,450,992 B1 | 9/2002 | Cassidy, Jr. | | 2003/0069548 A1 | 4/2003 | Connelly et al. |
| 6,488,663 B1 | 12/2002 | Steg | | 2003/0105430 A1 | 6/2003 | Lavi et al. |
| 6,517,517 B1 | 2/2003 | Farrugia et al. | | 2003/0109829 A1 * | 6/2003 | Mogensen et al. ..... 604/164.01 |
| 6,520,938 B1 | 2/2003 | Funderburk et al. | | 2003/0125669 A1 | 7/2003 | Safabash et al. |
| D472,316 S | 3/2003 | Douglas et al. | | 2003/0125678 A1 | 7/2003 | Swenson et al. |
| D472,630 S | 4/2003 | Douglas et al. | | 2003/0130619 A1 | 7/2003 | Safabash et al. |
| 6,572,586 B1 | 6/2003 | Wojcik | | 2003/0139704 A1 | 7/2003 | Lin |
| 6,579,267 B2 | 6/2003 | Lynch et al. | | 2003/0158520 A1 | 8/2003 | Safabash et al. |
| 6,582,397 B2 | 6/2003 | Alesi et al. | | 2003/0176843 A1 | 9/2003 | Wilkinson |
| 6,595,962 B1 | 7/2003 | Perthu | | 2003/0181863 A1 | 9/2003 | Davis et al. |

| | | | | | | |
|---|---|---|---|---|---|---|
| 2003/0181868 A1 | 9/2003 | Swenson | | 2006/0129123 A1 | 6/2006 | Wojcik |
| 2003/0181873 A1 | 9/2003 | Swenson | | 2006/0135908 A1 | 6/2006 | Liniger et al. |
| 2003/0181874 A1 | 9/2003 | Bressler et al. | | 2006/0173413 A1 | 8/2006 | Fan |
| 2003/0187394 A1 | 10/2003 | Wilkinson et al. | | 2006/0184104 A1 | 8/2006 | Cheney, II et al. |
| 2003/0187395 A1 | 10/2003 | Wilkinson et al. | | | | |
| 2003/0199823 A1 | 10/2003 | Bobroff et al. | | FOREIGN PATENT DOCUMENTS | | |
| 2003/0216686 A1 | 11/2003 | Lynch et al. | | DE | 299 05 072 U1 | 9/1999 |
| 2003/0225373 A1 | 12/2003 | Bobroff et al. | | DE | 203 20 207 U1 | 11/2004 |
| 2003/0225374 A1 | 12/2003 | Mathiasen | | DK | WO 01/72353 A2 | 10/2001 |
| 2003/0229308 A1 | 12/2003 | Tsals et al. | | DK | 1 360 970 A1 | 11/2003 |
| 2003/0229316 A1 | 12/2003 | Hwang et al. | | DK | 1 475 113 A1 | 11/2004 |
| 2004/0002682 A1 | 1/2004 | Kovelman et al. | | EP | 0 239 244 B1 | 2/1987 |
| 2004/0006316 A1 | 1/2004 | Patton | | EP | 0 290 176 A1 | 11/1988 |
| 2004/0026840 A1 | 2/2004 | Eckel et al. | | EP | 0 451 040 A1 | 10/1991 |
| 2004/0044306 A1 | 3/2004 | Lynch et al. | | EP | 0 544 837 B1 | 6/1993 |
| 2004/0049159 A1 | 3/2004 | Barrus et al. | | EP | 0 651 662 B1 | 5/1995 |
| 2004/0068231 A1 | 4/2004 | Blondeau | | EP | 0 657 184 B1 | 6/1995 |
| 2004/0087913 A1 | 5/2004 | Rogers et al. | | EP | 0 714 631 B1 | 6/1996 |
| 2004/0111068 A1 | 6/2004 | Swenson | | EP | 0 744 183 A2 | 11/1996 |
| 2004/0112781 A1 | 6/2004 | Hofverberg et al. | | EP | 0 747 006 A1 | 12/1996 |
| 2004/0116865 A1 | 6/2004 | Bengtsson | | EP | 0 688 232 B1 | 12/1998 |
| 2004/0138612 A1 | 7/2004 | Shermer et al. | | EP | 0 956 879 A1 | 11/1999 |
| 2004/0138620 A1 | 7/2004 | Douglas et al. | | EP | 0 615 768 A2 | 12/1999 |
| 2004/0143216 A1 | 7/2004 | Douglas et al. | | EP | 1 086 718 A1 | 3/2001 |
| 2004/0143218 A1 | 7/2004 | Das | | EP | 1 125 593 A1 | 8/2001 |
| 2004/0158202 A1 | 8/2004 | Jensen | | EP | 0 775 501 B1 | 6/2002 |
| 2004/0158207 A1 | 8/2004 | Hunn et al. | | EP | 1 329 233 A1 | 7/2003 |
| 2004/0162518 A1 | 8/2004 | Connelly et al. | | EP | 1 360 970 A1 | 11/2003 |
| 2004/0171989 A1 | 9/2004 | Horner et al. | | EP | 1 380 315 A1 | 1/2004 |
| 2004/0178098 A1 | 9/2004 | Swenson et al. | | EP | 0 956 879 A1 | 7/2004 |
| 2004/0186446 A1 | 9/2004 | Ohshima | | EP | 1 475 113 A1 | 11/2004 |
| 2004/0199123 A1 | 10/2004 | Nielson | | FR | 2725902 A1 | 10/1994 |
| 2004/0204687 A1 | 10/2004 | Mogensen et al. | | GB | 478803 | 1/1938 |
| 2004/0204690 A1 | 10/2004 | Yashiro et al. | | GB | 906574 | 9/1962 |
| 2004/0215151 A1 | 10/2004 | Marshall et al. | | GB | 2 088 215 A | 6/1982 |
| 2004/0220528 A1 | 11/2004 | Garcia, Jr. | | JP | A-03-191965 A | 8/1991 |
| 2004/0236284 A1 | 11/2004 | Hoste et al. | | JP | 7051251 A | 11/1995 |
| 2004/0238392 A1 | 12/2004 | Peterson et al. | | JP | A-08-187286 A | 7/1996 |
| 2004/0243065 A1 | 12/2004 | McConnell et al. | | JP | A-10-179734 A | 7/1998 |
| 2004/0254433 A1 | 12/2004 | Bandis et al. | | JP | 2002-028246 A | 1/2002 |
| 2004/0260235 A1 | 12/2004 | Douglas | | WO | WO 81/01795 A1 | 7/1981 |
| 2004/0260250 A1 | 12/2004 | Harris et al. | | WO | WO 82/03558 A1 | 10/1982 |
| 2005/0035014 A1 | 2/2005 | Cane | | WO | WO 9204062 A1 | 3/1992 |
| 2005/0043687 A1 | 2/2005 | Mogensen et al. | | WO | WO 93/05840 A2 | 4/1993 |
| 2005/0075606 A1 | 4/2005 | Botich | | WO | WO 96/20021 A1 | 7/1996 |
| 2005/0101910 A1 | 5/2005 | Bowman et al. | | WO | WO 96/032981 A1 | 10/1996 |
| 2005/0101912 A1 | 5/2005 | Faust et al. | | WO | WO 98/58693 A1 | 12/1998 |
| 2005/0101932 A1 | 5/2005 | Cote et al. | | WO | WO 99/07435 A1 | 2/1999 |
| 2005/0101933 A1 | 5/2005 | Marrs et al. | | WO | WO 99/33504 A1 | 7/1999 |
| 2005/0107743 A1 | 5/2005 | Fangrow, Jr. | | WO | WO 00/02614 A1 | 1/2000 |
| 2005/0113761 A1 | 5/2005 | Faust et al. | | WO | WO 00/03757 A1 | 1/2000 |
| 2005/0119611 A1 | 6/2005 | Marano-Ford et al. | | WO | WO 00/44324 A1 | 8/2000 |
| 2005/0119619 A1 | 6/2005 | Haining | | WO | WO 01/30419 A2 | 5/2001 |
| 2005/0119637 A1 | 6/2005 | Lundgren et al. | | WO | WO 01/68180 A1 | 9/2001 |
| 2005/0124936 A1 | 6/2005 | Mogensen et al. | | WO | WO 01/72353 A2 | 10/2001 |
| 2005/0131347 A1 | 6/2005 | Marano-Ford et al. | | WO | WO 01/93926 A2 | 12/2001 |
| 2005/0159709 A1 | 7/2005 | Wilkinson | | WO | WO 02/081012 A2 | 10/2002 |
| 2005/0215979 A1 | 9/2005 | Konerup et al. | | WO | WO 02/094352 A2 | 11/2002 |
| 2005/0251098 A1 | 11/2005 | Wyss et al. | | WO | WO 02/100457 A2 | 12/2002 |
| 2005/0256456 A1 | 11/2005 | Marano-Ford et al. | | WO | WO 02/102442 A1 | 12/2002 |
| 2005/0261629 A1 | 11/2005 | Marano-Ford et al. | | WO | WO 02/068014 A3 | 1/2003 |
| 2005/0277892 A1 | 12/2005 | Chen | | WO | WO 03/015860 A1 | 2/2003 |
| 2005/0283114 A1 | 12/2005 | Bresina et al. | | WO | WO 03/026728 A1 | 4/2003 |
| 2006/0015063 A1 | 1/2006 | Butikofer et al. | | WO | WO 2004/030726 A1 | 4/2004 |
| 2006/0030815 A1 | 2/2006 | Csincsura et al. | | WO | WO 2005/004973 A1 | 1/2005 |
| 2006/0041224 A1 | 2/2006 | Jensen | | WO | WO 2005/046780 A1 | 5/2005 |
| 2006/0069351 A9 | 3/2006 | Safabash et al. | | WO | WO 2005/068006 A1 | 7/2005 |
| 2006/0095003 A1 | 5/2006 | Marano-Ford et al. | | | | |
| 2006/0095014 A1 | 5/2006 | Ethelfeld | | * cited by examiner | | |

CONTAINER FOR DISPOSABLE NEEDLE OR CANNULA

The present invention relates to a container for a disposable needle. More particularly, the invention refers to a container for a disposable needle for drug infusion, which container makes needle placement through a patient's skin easier.

As known, several medical treatments exploit subcutaneous infusion of liquid drugs: the drug flows through a hose connected to a needle placed through the patient's skin and it is directly delivered under the skin through said needle. Alternatively, insertion needles are employed for placement through the patient's skin of a soft and relatively flexible tubular cannula, followed by insertion needle removal and subsequent infusion of medical fluid to the patient directly through the cannula. In some cases, the patient himself/herself is to administer the drug. For instance, many diabetic patients self-administer insulin, in the form of controlled and prolonged infusion.

Clearly, many patients have no medical knowledge and therefore they may be reluctant to place the needle or cannula through their skin or inexpert in doing so. Thus, it is necessary to provide means allowing automatic placement, so as to prevent the patient's lack of skill or hesitation from resulting in an incorrect needle or cannula placement, with possible dangerous consequences.

Devices of this kind, which can be employed for the subcutaneous infusion of a liquid drug either through a needle or through a soft cannula, already exist and one of them is disclosed in U.S. Pat. No. 6,093,172.

According to the teaching of the above mentioned patent, a device for needle placement comprises a cylinder, the lower portion of which can receive the outward-directed needle and related hose, ready for placement through the patient's skin. Said cylinder internally includes a spring that can be brought into a loaded condition and, on its upper portion, a trigger that is to release said spring. By depressing the trigger, the spring is released so as to outward project, more particularly through the patient's skin, the needle located in the lower portion of the device. Once the needle is placed through the skin, a slight traction is sufficient to retract the device and leave the needle in place, in the correct position.

A problem with such kind of devices is that the patient is to provide for the correct introduction of the infusion set into the lower portion of the cylinder, to ensure a correct needle positioning.

It is a main object of the present invention to provide a container within which a needle and the related hose or, alternatively, a cannula, are already correctly positioned, so that the patient only has to place said container against his/her skin and to release the needle or cannula through a simple movement.

Another drawback of such known devices is that, while the needle is being placed inside the device, the user risks to prickle himself/herself while handling the needle. Moreover, at such step, the needle is exposed to the outside environment and in particular to germs and bacteria.

Thus, it is another object of the present invention to provide a container for a disposable needle or cannula that does not result in the risk for the user to prickle himself/herself during use and that allows maintaining hygiene and safety in respect of possible contamination by external agents.

A container for a disposable needle intended to facilitate needle or cannula placement through a patient's skin is disclosed in U.S. Pat. No. 6,093,172.

The above and other objects of the invention are achieved by a container as defined in the appended claims.

The container according to the invention has the appearance of a small housing of plastic material, already containing the needle connected with the related hose or, alternatively, the end of the cannula connected with the related insertion needle, and protected from the surrounding environment by means of a protecting film.

After said film has been removed and the container base has been placed against the skin, a simple push is sufficient to release the needle and pierce the skin.

Once the needle has been placed through the skin, the container can be removed by slightly pulling it, without risks of displacing the needle from the correct position.

If the drug is to be delivered to the patient directly through a soft cannula, the insertion needle of said cannula can be removed together with the container, without displacing the cannula.

Advantageously, the construction of a disposable device affords maximum simplicity of use and maximum hygiene.

A number of embodiments of the invention will be disclosed in greater detail with reference to the accompanying drawings, wherein the container according to the invention is employed for the insertion of a needle through a patient's skin. However, as already mentioned, the container according to the invention can be similarly used for the insertion of a soft cannula through a patient's skin.

Figure 1:
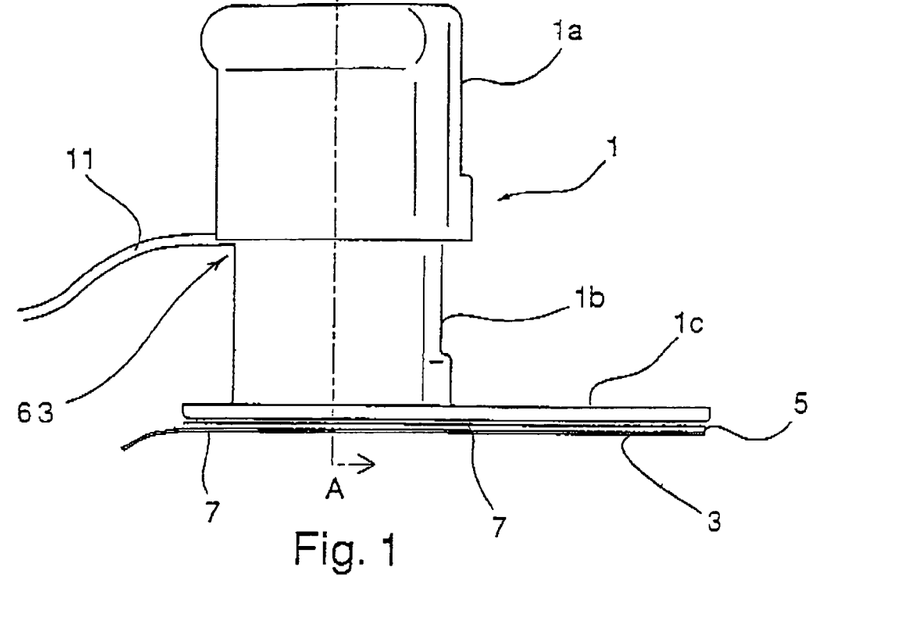
FIG. 1 is a side view of the container according to a first embodiment of the invention, shown before use.

Referring to FIG. 1, the container according to a first embodiment of the present invention comprises a cylindrical housing 1, in which there is defined a cap 1a axially slidable relative to a sleeve 1b when a sufficient pressure is exerted on said cap 1a.

Said cap 1a moreover has an inner diameter slightly exceeding the outer diameter of sleeve 1b, so as to allow sleeve 1b to be received within cap 1a when the latter has been wholly depressed.

Sleeve 1b is integral with a base 1c intended for placing the container against the patient's skin, in the area where a L-shaped needle is to be inserted.

A hose 11, intended to supply the needle located within housing 1 with the drug, as it will be better disclosed hereinafter, radially comes out from sleeve 1b through an axial slit 63.

It is to be noted that said L-shaped needle with its related hose can be replaced by a soft cannula provided with an insertion needle of the type shown above captioned U.S. Pat. No. 6,093,172. Said cannula is a hollow tube made from a soft and flexible material, which can be bent into a desired configuration. In order to insert the cannula through a patient's skin, an insertion needle is introduced in the free end of the cannula and used for piercing the patient's skin and driving through the patient's skin said end of said cannula. The insertion needle is then removed, the cannula is bent into a L-shaped configuration for purpose of practicalness so as to adhere to the patient's skin and the drug is infused through the cannula. It is evident that, within the scope of the invention, the above disclosed cannula, together with the associated insertion needle, is equivalent to the aforesaid L-shaped needle and, for this reason, it will not be further described.

Outside housing 1, a removable film 3 is applied onto base 1c, to protect an adhesive gauze 5 placed between said film and base 1c and weakly adhering to base 1c in correspondence of a set of circular portions 7.

Figure 2:
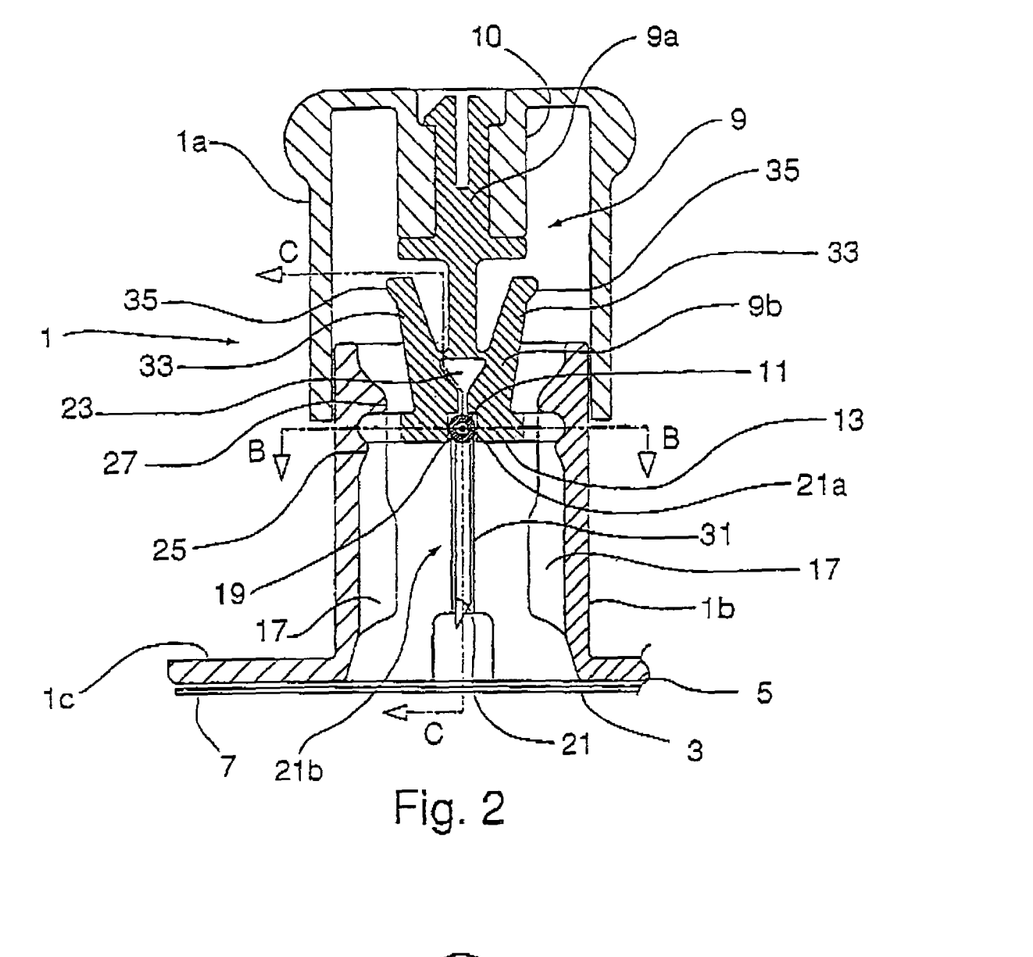
FIG. 2 is a cross-sectional view taken along line A-A in FIG. 1.

Referring now to FIG. 2, the container according to said first embodiment of the invention comprises, within said housing 1, a retaining member 9 comprising a securing portion 9a directed towards cap 1a and a retaining portion 9b directed towards sleeve 1b.

Securing portion 9a is firmly held inside an axial cylindrical hub 10 extending within cap 1a and integral therewith. Retaining portion 9b axially extends inside the container and ends, at its end remote from said securing portion 9a, with a plate 13 transversally arranged relative to the axis of retaining member 9.

Figure 4:
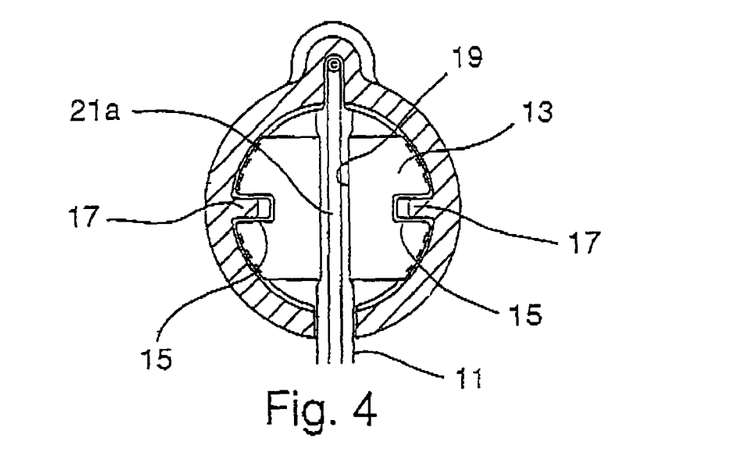
FIG. 4 is a cross-sectional view taken along line B-B in FIG. 2.

As better shown in FIG. 4, said plate 13 has a substantially circular shape and has a pair of diametrically opposite radial grooves 15, through which corresponding axial projections 17 formed within sleeve 1b pass. Said projections are arranged to guide the axial sliding of plate 13, and consequently of member 9, when cap 1a is pressed against sleeve 1b.

Still with reference to FIG. 4, said plate 13 further comprises a groove 19, diametrically crossing the whole plane of plate 13, perpendicularly to radial grooves 15. Groove 19 retains inlet branch 21a of an L-shaped needle 21 for the infusion of the drug, housed inside the container.

Turning back to FIG. 2, said groove 19 axially extends inside plate 13 and retaining element 9b and widens, at its end, into a radial hollow 23, thereby to define two diametrically opposite portions of said plate 13. As it will be explained thereinafter, said portions can be deformed to release needle 21 once cap 1a has been depressed.

Two circumferential rims 25 and 27, respectively, are formed on the internal wall of sleeve 1b to keep plate 13 in engagement against sleeve 1b, thereby preventing cap 1a from sliding until a force sufficient to overcome the resistance of outermost rim 25 relative to said cap 1a is exerted against said cap.

Figure 5:
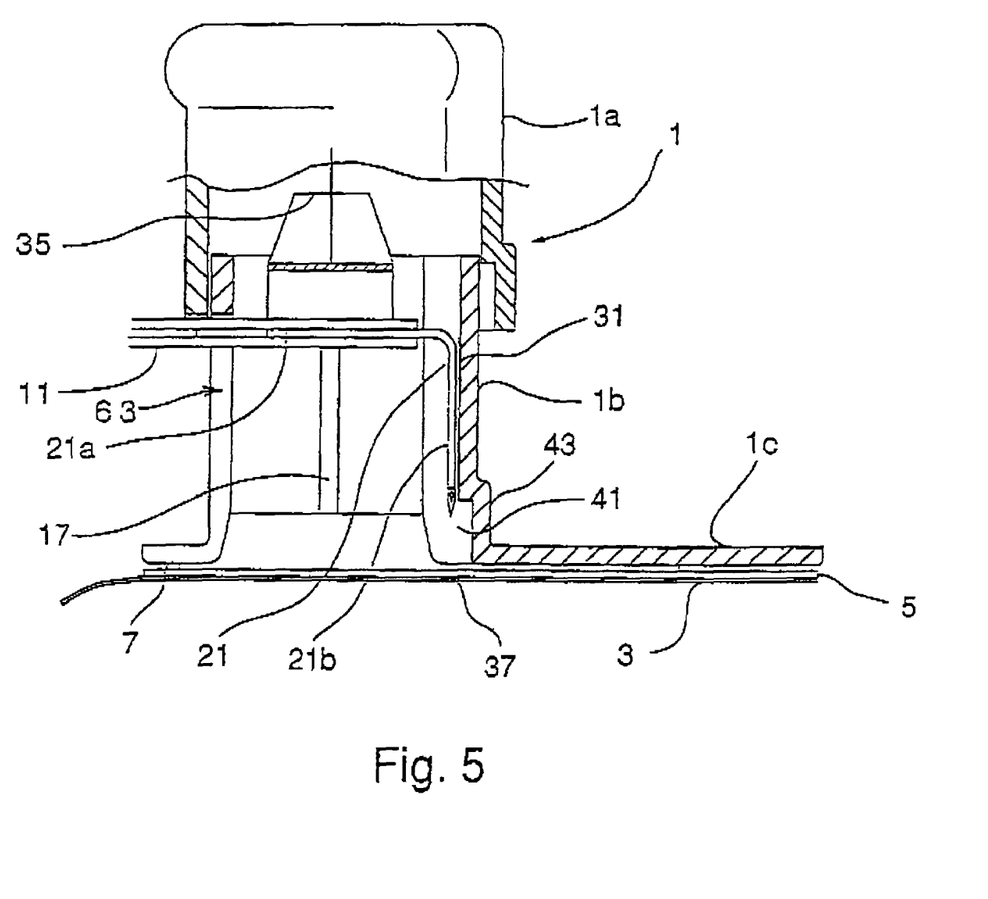
FIG. 5 is a cross-sectional view taken along line C-C in FIG. 2.

With reference to FIG. 5, the internal wall of sleeve 1b comprises an axial groove 31 housing outlet branch 21b of L-shaped needle 21.

Said sleeve 1b further has, at the end of said axial groove 31, a widened portion 41 in correspondence of base 1c, to prevent branch 21b of needle 21 from sticking into the wall of sleeve 1b while advancing towards the outside through opening 37 provided in gauze 5. Cap 1a has a corresponding widening 43 to receive the outer projection defined by said widened portion 41 when sleeve 1b is completely received within cap 1a.

Turning back to FIG. 2, retaining portion 9b further comprises a pair of diametrically opposite fins 33 upward projecting from plate 13 and diverging towards cap 1a. Said fins 33 end with a convex portion 35, interfering with axial projections 17 when cap 1a is depressed and retaining member 9 is made to slide along sleeve 1b, thereby disengaging plate 13 from rim 25 and bringing the container to the position shown in FIG. 3.

Figure 3:
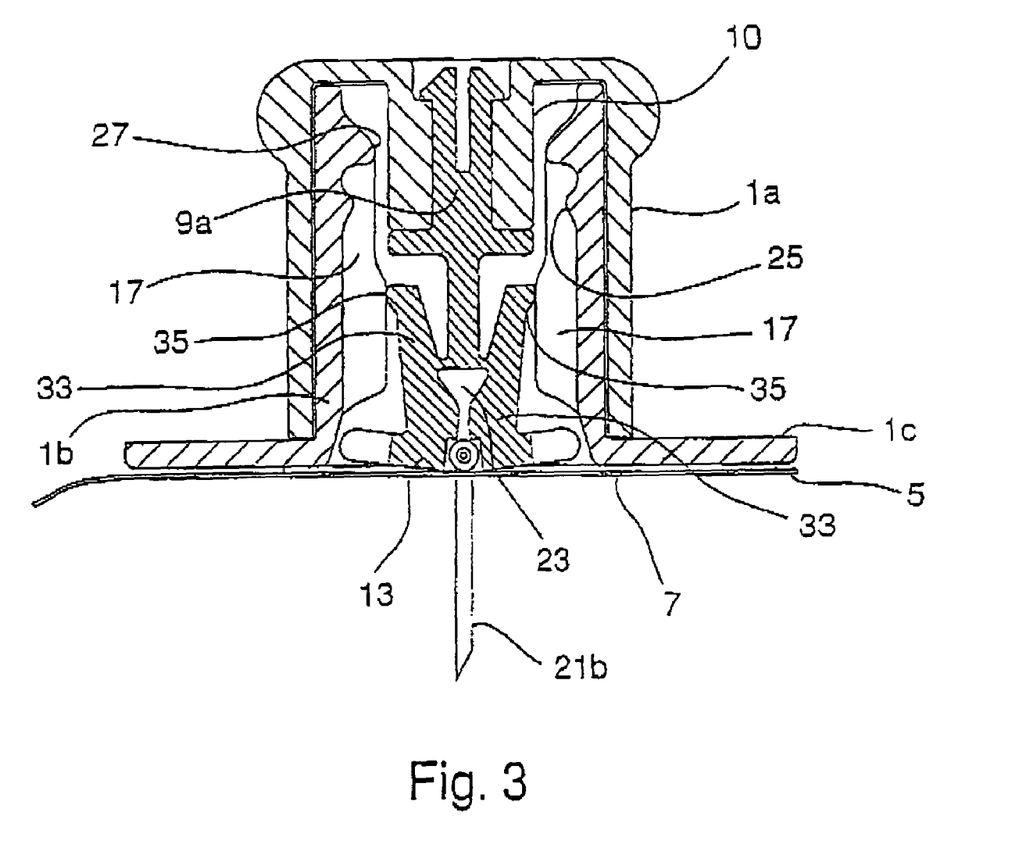
FIG. 3 is a cross-sectional view taken along line A-A in FIG. 1, after needle insertion.

Referring now to FIG. 3, when cap 1a is completely lowered against sleeve 1b, retaining member 9 is arranged with plate 13 against the inner face of gauze 5, and branch 21b of L-shaped needle 21 will be completely placed through the patient's skin after having passed through opening 37 in gauze 5.

Figure 6:
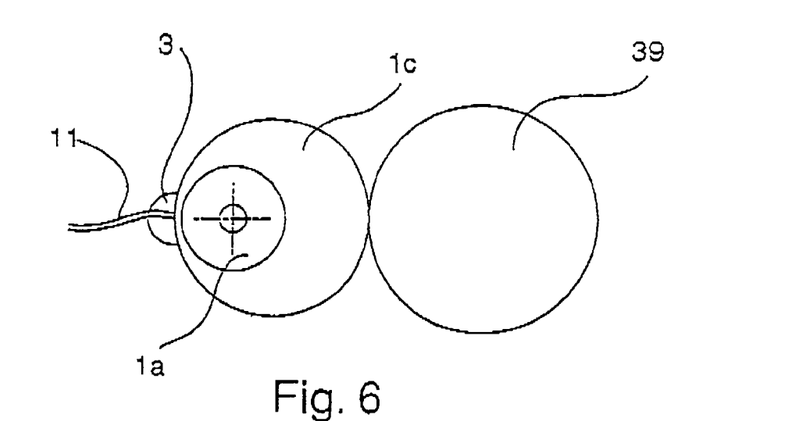
FIG. 6 is a top view of the container according to said first embodiment of the invention.

Referring now to FIG. 6, gauze 5 is joined to a second adhesive gauze 39, which in turn is protected by a respective removable adhesive film. The border of second gauze 39 can be folded on gauze 5 when needle 21 has been inserted and the container has been removed. Thus, the patient can advantageously cover the area of gauze 5 and branch 21a of L-shaped needle 21 by said second gauze 39, whereby only the border of gauze 39 is externally visible and the area occupied by the needle is thus protected.

The operation of the container according to said first embodiment is as follows: starting from the configuration shown in FIG. 2, protecting film 3 is removed and adhesive gauze 5 is made to adhere to the patient's skin in the area where needle 21 is to be inserted. Pushing cap 1a towards base 1c results, once the resistance of rim 25 has been overcome, in the release of plate 13 and the sliding of cap 1a on sleeve 1b. During this step, needle 21 is placed through the patient's skin and, at the same time, is released from retaining member 9 because of the deformation of plate 13 due to the pressure radially exerted by projections 17 onto fins 33. The container has thus taken the configuration shown in FIG. 3 and it can be removed, while leaving the needle in place thanks to the weak adhesion between base 1c and gauze 5 if compared with the adhesion between gauze 5 and the patient's skin. Subsequently, the protecting film of second gauze 39 can be removed therefrom and gauze 39 can be folded on and made to adhere to gauze 5.

Referring now to FIGS. 7 to 11, a second embodiment of the invention is shown, which differs from the first embodiment in particular in respect of the structure of the needle-retaining member.

Figure 7:
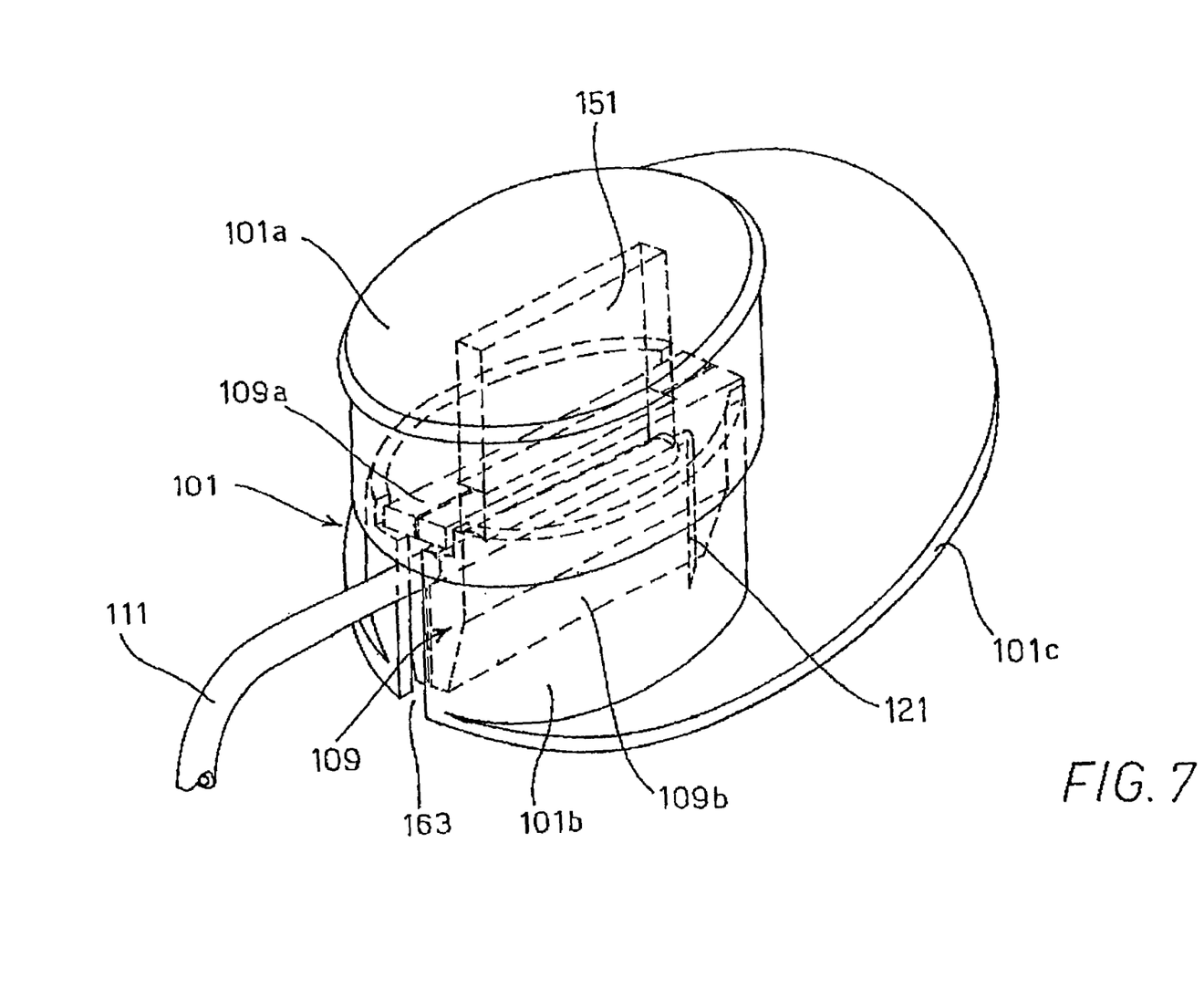
FIG. 7 is an overall perspective view of the container according to a second embodiment of the invention, shown before use.
Figure 8:
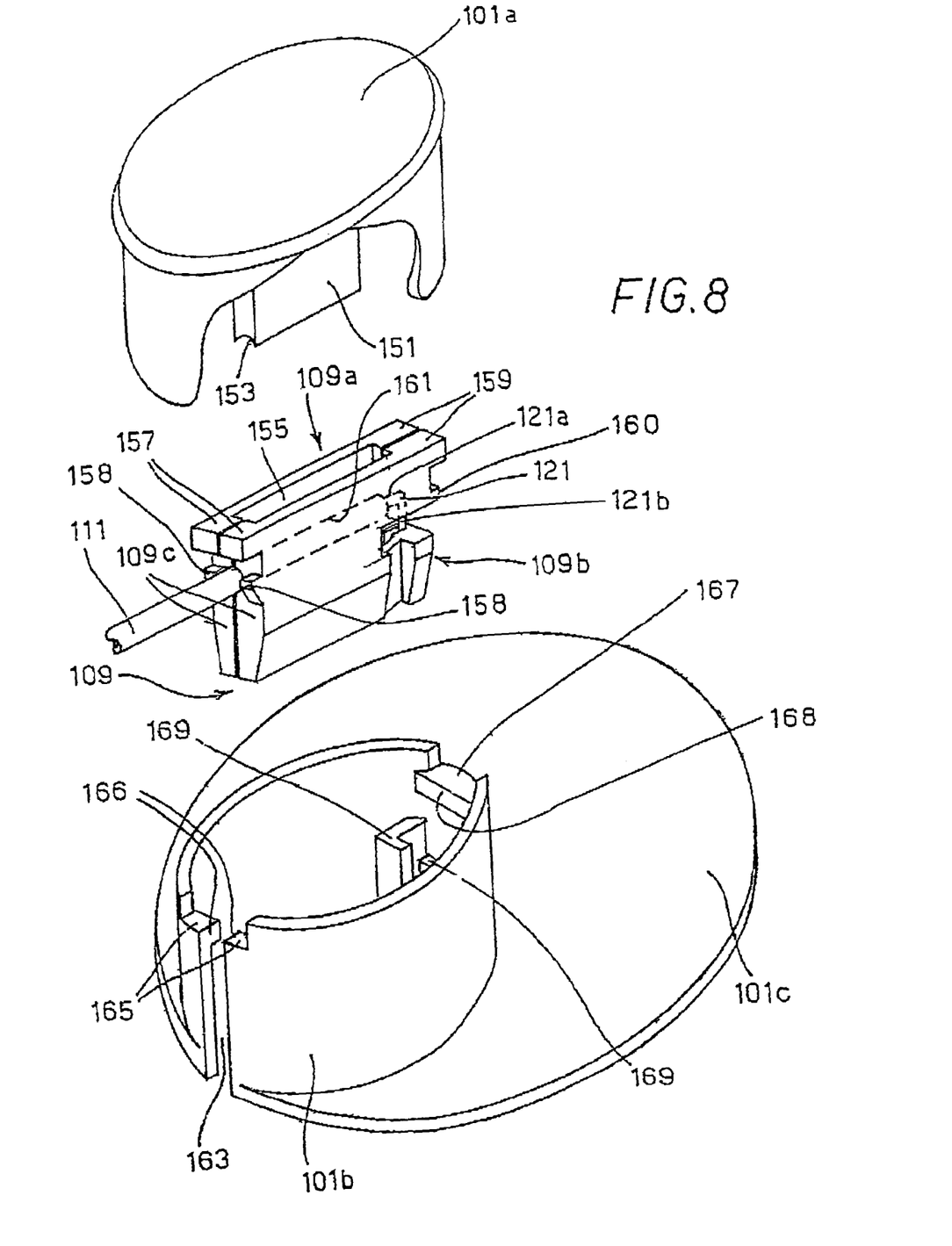
FIG. 8 is an exploded view of the container shown in FIG. 7.

In this second embodiment, the container comprises a cylindrical housing 101, in which a cap 101a and a sleeve 101b are defined. The sleeve has a slightly smaller diameter, so that, when a sufficient pressure is exerted on cap 101a, the latter is axially slidable relative to sleeve 101b and can internally receive the sleeve. Said sleeve 101b is integral with a base 101c intended for placing the container against the patient's skin.

Slightly projecting circumferential rims could be provided on the inner surface of the base of cap 101a and on the outer surface of the edge of sleeve 101b remote from base 101c, respectively. Thanks to the co-operation between said circumferential rims, when housing 101 is assembled, said cap 101a is axially slidable on sleeve 101b but it cannot be accidentally separated therefrom.

Moreover, an annular band, e.g. of plastic material, could be applied around sleeve 101b to prevent cap 101a from accidentally sliding relative to sleeve 101b. Said band can be easily removed by the user before use.

A hose 111 radially comes out from sleeve 101b through an axial slit 163. Said hose is intended to deliver the drug to an L-shaped needle 121, located within housing 101 and comprising an inlet branch 121a, onto which the hose is fitted, and an outlet branch 121b, intended to be at least partly placed through the patient's skin. Said L-shaped needle 121 is housed within a retaining member 109, contained within housing 101.

Said retaining member 109 comprises a securing portion 109a and a retaining portion 109b and consists of two coupled half-shells 109c, shaped so as to define therebetween a cavity 161 capable of receiving said needle 121.

Securing portion 109a comprises two shoulders 157, 159, which are received into corresponding recesses 165, 167 formed in the edge of sleeve 101b remote from base 101c.

More particularly, recess 165 formed in correspondence with slit 163 is so sized that its edges resiliently press against shoulder 157 of retaining member 109, whereas the opposite recess 167 is oversized with respect to the corresponding shoulder 159 in said member 109, so that a clearance is left.

In the alternative, a pair of facing resilient members could be formed on the internal surface of said sleeve 101b, which members radially project towards the centre of said sleeve to such an extent that they press against half-shells 109c of said member 109.

Advantageously, radial projections 166, 168 are provided on the inner surface of sleeve 101b in correspondence with recesses 165, 167 and are firmly held between said shoulders 157, 159 and corresponding teeth 158, 160 formed in securing portion 109a of said retaining member 109. In such manner, retaining member 109 is axially joined to sleeve 101b.

Furthermore, a recess 155, extending up to cavity 161, is defined in securing portion 109a, to receive a projection 151 centrally provided inside cap 101a. Preferably, end 153 of said projection 151 is so shaped that it conforms to the curved profile of hose 111.

Two facing L-shaped axial projections 169, diametrically opposed and parallel to slit 163, are provided inside sleeve 101b and they form a seat for the portion of said retaining member 109 receiving outlet branch 121b of needle 121.

Figure 9:
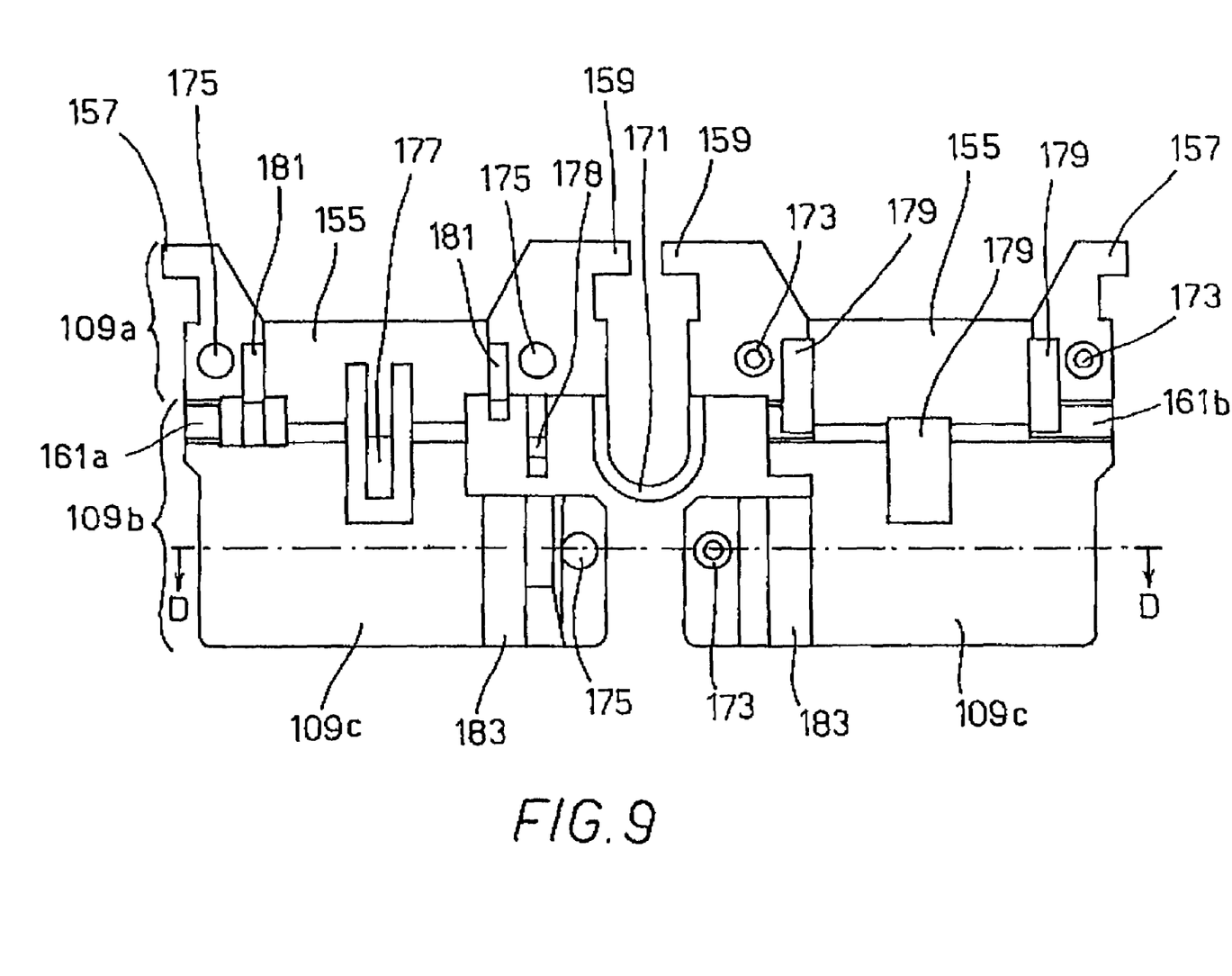
FIG. 9 is a plan view of the needle-retaining member in the container shown in FIG. 7, shown before assembling.
Figure 10:
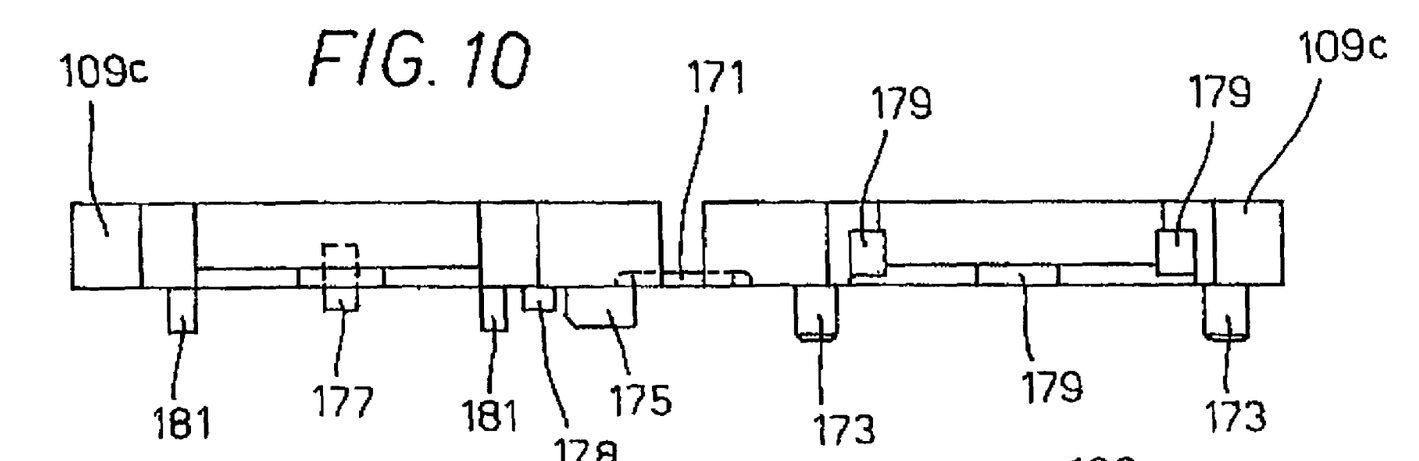
FIG. 10 is a side view of the needle-retaining member shown in FIG. 9.
Figure 11:
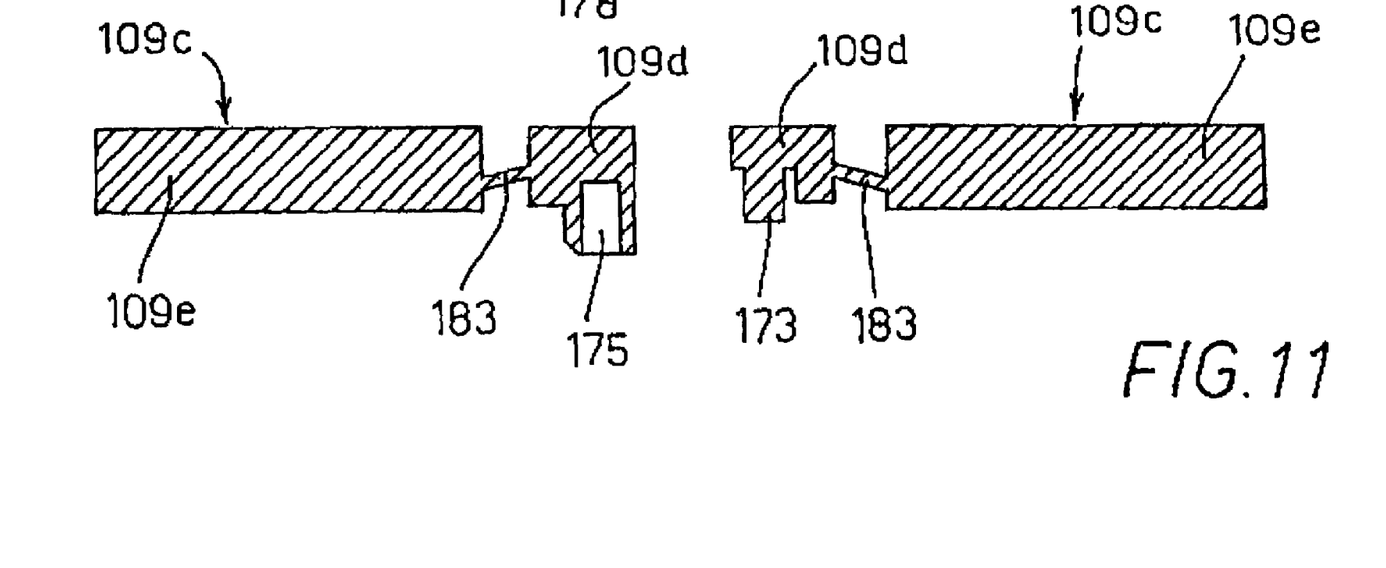
FIG. 11 is a cross-sectional view, taken along line D-D, of the needle-retaining member shown in FIG. 9.

FIGS. 9 to 11 show in detail retaining member 109.

Advantageously, said retaining member 109 consists of two facing half-shells 109c, whereby positioning of needle 121 is particularly easy: indeed, it will be sufficient to place said needle between said half-shells 109c and then to join them, thereby blocking the needle therebetween. Said half-shells 109c are preferably formed by moulding into a single element, and therefore they are advantageously joined by a flexible member 171 making their assembling easier.

One of said half-shells 109c comprises three pins 173 engaging corresponding holes 175 in the other half-shell 109c, thereby assisting in correctly aligning both half-shells 109c at the assembling and, subsequently, in keeping them joined.

Both half-shells 109c have a groove 161a, 161b defining cavity 161 when half-shells 109c are joined.

Inlet branch 121a of needle 121, on which hose 111 is fitted, is retained inside cavity 161 thanks to the co-operation between a pair of support projections 177, 178 and a pair of rigid tongues 181 provided on one of half-shells 109c and housed in respective seats 179 in the other half-shell.

One of said support projections, 178, is suitably arranged on one half-shell 109c in correspondence of the bend between inlet and outlet branches 121a, 121b of needle 121. When the retaining member 109 is assembled, said projection 178 prevents, by co-operating with the surface of the facing half-shell 109, needle removal from housing 101.

As shown in FIG. 11, retaining portion 109b of each half-shell 109c is divided into two sections 109d, 109e connected by a flexible connecting member 183 allowing limited relative displacements of said sections.

When half-shells 109c are joined together, sections 109e in the respective half-shells adhere to each other, whereas a passage for outlet branch 121b of needle 121 is defined between sections 109d.

In this second embodiment, insertion and release of the needle take place as follows. When pushing cap 101a with sufficient force towards container base 101c, projection 151 presses against hose 111 and, by overcoming the resistance of pins 173 and the elastic resistance of sleeve 101b, said projection forces half-shells 109c apart. Sections 109d of said half-shells 109c cannot be separated, since they are rigidly retained by L-shaped projections of sleeve 101b, so that the passage for outlet branch 121b of needle 121 defined therebetween keeps unchanged. On the contrary, sections 109e of said half-shells can be spaced apart, by overcoming the elastic resistance of the edges of recess 165 in sleeve 101b. In such manner, hose 111 can pass through half-shells 109c along slit 163, while needle 121 is guided between facing sections 109d of half-shells 109c, until its outlet branch 121b becomes completely placed through the patient's skin.

Similarly to what described in connection with the first embodiment of the invention, also in this second embodiment the container can comprise, outside housing 101 and against base 101c, an adhesive gauze 5 weakly adhering to base 101c in correspondence of a set of circular portions. Thus, gauze 5 can remain adhering to the patient's skin after needle 121 has been placed through the patient's skin and the container has been removed. Said adhesive gauze 5 could be possibly joined with a second, protecting adhesive gauze which could be folded onto said first gauze after container removal.

It is clear that the above description has been given only by way of non-limiting example and that changes and modifications are possible without departing from the scope of the invention.

In particular, as already mentioned, even if the above description has been given with reference to the insertion of a needle through which the drug coming from a related hose is delivered to a patient, the container according to the invention can also be used for the insertion through a patient's skin of a cannula provided with an insertion needle when the drug is to be delivered to the patient directly through said cannula.

What is claimed is:

1. A container for facilitating placement of a medical device through a patient's skin, the container comprising:
    a cylindrical housing in which there are defined a cap and a sleeve, said sleeve including a resting base having a planar surface configured for placement against a patient's skin, said cap surrounding at least a portion of said sleeve and being axially slidable relative to said sleeve to substantially encase said sleeve when a sufficient pressure is exerted on said cap;
    a retaining member located within said housing, said retaining member having a needle secured thereto;
    a releasing member for releasing said needle from said retaining member when said cap is made to slide on said sleeve, thereby allowing the placement of said needle under the patient's skin and the subsequent removal of said container;
    wherein the container is disposable and upon exertion of said pressure on said cap the force resulting from said pressure is transferred to said needle so that said needle is placed through the patient's skin by means of said pressure exerted on said cap.

2. A container as claimed in claim 1, wherein said base has, on an outer face, a gauze adhering to said base, said gauze comprising an adhesive having a removable protecting film thereon.

3. A container as claimed in claim 2, wherein said gauze is joined to said base in circular portions.

4. A container for facilitating placement of a medical device through a patient's skin, the container comprising:
   a cylindrical housing in which there are defined a cap and a sleeve, said sleeve including a resting base having a planar surface configured for placement against a patient's skin, said cap being axially slidable relative to said sleeve when a sufficient pressure is exerted on said cap;
   a retaining member located within said housing, said retaining member having a needle secured thereto;
   a releasing member for releasing said needle from said retaining member when said cap is made to slide on said sleeve, thereby allowing the placement of said needle under the patient's skin and the subsequent removal of said container;
   wherein the container is disposable and upon exertion of said pressure on said cap the force resulting from said pressure is transferred to said needle so that said needle is placed through the patient's skin by means of said pressure exerted on said cap and
   wherein said sleeve has an axial slit through which a hose extends radially and along which said hose is slidable when said cap is made to slide on said sleeve.

5. A container for facilitating placement of a medical device through a patient's skin, the container comprising:
   a cylindrical housing in which there are defined a cap and a sleeve, said sleeve including a resting base having a planar surface configured for placement against a patient's skin, said base having, on an outer face, a gauze adhering to said base, said gauze comprising an adhesive having a removable protecting film thereon, said cap being axially slidable relative to said sleeve when a sufficient pressure is exerted on said cap;
   a retaining member located within said housing, said retaining member having a needle secured thereto;
   a releasing member for releasing said needle from said retaining member when said cap is made to slide on said sleeve, thereby allowing the placement of said needle under the patient's skin and the subsequent removal of said container;
   wherein the container is disposable and upon exertion of said pressure on said cap the force resulting from said pressure is transferred to said needle so that said needle is placed through the patient's skin by means of said pressure exerted on said cap and
   wherein said needle is an L-shaped needle comprising a drug inlet branch transversally arranged within said housing and an axially arranged drug outlet branch, said inlet branch being connected to a hose radially extending from said container.

6. A container as claimed in claim 5, wherein said retaining member includes a securing portion directed toward said cap and a retaining portion directed toward said sleeve, said securing portion being firmly held inside an axial cylindrical hub extending within the cap and integral therewith, and said retaining portion axially extending within the housing and ending, at its end remote from said securing portion, with a plate transversally arranged relative to the axis of the retaining member, said plate being engaged against said sleeve so as to allow sliding of said cap on said sleeve when said plate is released from said sleeve.

7. A container as claimed in claim 6, wherein said plate has a substantially circular shape and comprises a pair of diametrically opposite radial grooves for the passage of corresponding axial projections formed within the sleeve and arranged to guide the axial sliding of the plate and the retaining member, when said cap is depressed.

8. A container as claimed in claim 7, wherein said plate comprises a groove, diametrically crossing the plane of the plate and retaining the inlet branch of the L-shaped needle for the infusion of the drug, said groove being arranged perpendicularly to said radial grooves.

9. A container as claimed in claim 8, wherein said groove retaining the needle axially extends inside the plate and the retaining member and widens at its end, into a radial hollow, thereby to define two diametrically opposite portions of said plate, which portions are deformable to release the needle retained in said groove.

10. A container as claimed in claim 9, wherein a pair of radially extending protrusions are formed on the internal wall of said sleeve to keep the plate in engagement with said sleeve, and wherein the internal wall of said sleeve comprises an axial groove through which the outlet branch of the L-shaped needle passes.

11. A container as claimed in claim 10, wherein said releasing member for releasing said needle from said retaining member comprises a pair of diametrically opposite fins, which are formed in the retaining portion of said retaining member and which project upwardly from the plate and diverge toward the cap, said fins ending with a convex portion interfering with said axial projections when the cap is depressed and the retaining member is made to slide along the sleeve for releasing the plate from the protrusions, so that, when the cap is completely lowered against the sleeve, the retaining member is arranged with the plate against the gauze and the branch of the L-shaped needle is completely placed through the patient's skin after having passed through an opening in the gauze.

12. A container as claimed in claim 5, wherein said retaining member comprises two coupled half-shells and includes a securing portion directed toward said cap and a retaining portion directed toward said sleeve, said retaining portion including a cavity between said half-shells for receiving said needle, and said securing portion comprising two shoulders, which are received into corresponding recesses formed in the edge of the sleeve remote from said base, and an axial recess extending up to said cavity.

13. A container as claimed in claim 12, wherein said sleeve comprises means for resiliently retaining said half-shells against each other.

14. A container as claimed in claim 12, wherein respective radial projections are provided on the inner surface of said sleeve in correspondence with the recesses, which projections co-operate with said shoulders and with respective teeth formed in the securing portion of said retaining member to axially join said retaining member to said sleeve.

15. A container as claimed in claim 12, wherein one of said half-shells comprises one or more pins engaging corresponding holes in the other half-shell when said half-shells are coupled to each other.

16. A container as claimed in claim 12, wherein the inlet branch of said needle is retained inside said cavity by co-operation between at least one support projection and at least one tongue provided on one of said half-shells and received in respective seats provided in the other half-shell.

17. A container as claimed in claim 16, wherein one of said support projections is configured to prevent transversal movements of said needle relative to said sleeve.

18. A container as claimed in claim 12, wherein the half-shells are divided into first sections and second sections connected by a flexible connecting member, said first sections being shaped to define therebetween a passage for the outlet branch of said needle when said half-shells are joined to each other.

19. A container as claimed in claim 18, wherein said sleeve comprises two facing L-shaped axial projections forming a seat for said first sections.

20. A container as claimed in claim 19, wherein said releasing member comprises a projection provided inside said cap and received within said recess, wherein said projection is configured to force apart said second sections of the half-shells of said retaining member and push the inlet branch of said needle toward the container base when said cap slides on said sleeve, until the complete placement of the outlet branch of said needle through the patient's skin.

21. A container as claimed in claim 11, further comprising a second gauze, protected by a respective removable adhesive film and joined with said first gauze, the second gauze being foldable on the first gauze when the needle has been inserted and the container has been removed, whereby the first gauze and the inlet branch of the needle can be covered leaving only said second gauze exposed.

22. A container as claimed in claim 20, further comprising a second gauze, protected by a respective removable adhesive film and joined with said first gauze, the second gauze being foldable on the first gauze when the needle has been inserted and the container has been removed, whereby the first gauze and the inlet branch of the needle can be covered leaving only said second gauze exposed.

23. A container for facilitating placement of a cannula of a medical device through a patient's skin, the container comprising:
   a housing comprising a cap telescopically slidable over a sleeve, said sleeve defining an axis therethrough and including a resting base configured for placement against said patient's skin, said cap being slidable between a first position and a second position along the axis of said sleeve, wherein said cap substantially encases the axial length of said sleeve when said cap is in said second position; and
   a retaining member located within said housing, said retaining member having a piercing member secured thereto, said piercing member extending at least partially through said cannula for transcutaneous placement of said cannula;
   wherein said piercing member is concealed within said sleeve when said cap is in said first position and exposed from said sleeve when said cap is in said second position;
   wherein upon exertion of said pressure on said cap, said cap slides axially toward said patient's skin along said sleeve so that said piercing member is placed through said patient's skin and an end of said cannula is transcutaneously inserted and said medical device is retained on the patient and said piercing member secured to said retaining member is removed.

24. The container of claim 23 wherein a force resulting from an insertion pressure exerted on said cap is transferred to said piercing member.

25. The container of claim 23 further comprising a projecting structure defining said retaining member and extending generally axially from an end portion of said cap within said sleeve.

26. The container of claim 25 wherein said piercing member is attached to said projecting structure.

27. The container of claim 23 wherein said base comprises an adhesive face configured for adhering said base to said patient's skin.

28. The container of claim 27 further comprising a gauze attached to said base, said gauze configured for adhering said base to said patient's skin.

29. The container of claim 28, wherein said gauze includes an opening for said piercing member.

30. The container of claim 27 further comprising a protective film for covering said adhesive face prior to adhering said base to said patient's skin.

31. A container for facilitating placement of a cannula of a medical device through a patient's skin, the container comprising:
   a housing comprising a care telescopically slidable over a sleeve, said sleeve defining an axis therethrough and including a resting base configured for placement against said patient's skin, said cap being slidable between a first position and a second position along the axis of said sleeve, wherein said care substantially encases the axial length of said sleeve when said care is in said second position; and
   a retaining member located within said housing, said retaining member having a piercing member secured thereto, said piercing member extending at least partially through said cannula for transcutaneous placement of said cannula; and
   a release member for releasing said piercing member from said retaining member;
   wherein said piercing member is concealed within said sleeve when said cap is in said first position and exposed from said sleeve when said care is in said second position; and
   wherein upon exertion of said pressure on said cap, said cap slides axially toward said patient's skin along said sleeve so that said piercing member is placed through said patient's skin and an end of said cannula is transcutaneously inserted and said medical device is retained on the patient and said piercing member secured to said retaining member is removed.

32. The container of claim 23, further comprising a releasable annular protector surrounding said at least a portion of said sleeve to prevent said cap from sliding relative to said sleeve.

33. The container of claim 23, wherein said sleeve extends distal to a tip of said piercing member prior to insertion of said piercing member.

34. The container of claim 23, wherein said sleeve further comprises a pair of guiding members to guide said cap relative to said sleeve when said cap is depressed.

35. The container of claims 23 wherein said piercing member is adapted to administer a drug.

* * * * *

UNITED STATES PATENT AND TRADEMARK OFFICE
CERTIFICATE OF CORRECTION

PATENT NO.         : 7,407,493 B2                                   Page 1 of 1
APPLICATION NO. : 10/872423
DATED              : August 5, 2008
INVENTOR(S)        : Mario Cane'

It is certified that error appears in the above-identified patent and that said Letters Patent is hereby corrected as shown below:

<u>On the Title Page</u>

On page 3, in column 1, line 63, delete "Roenborg et al." and substitute --Rønborg et al.-- in its place.

On page 3, in column 2, line 2, after "8/2003" delete "Halseth" and substitute --Halseth et al.-- in its place.

<u>In the Claims</u>

In column 10, in claim 31, line 4, after "comprising a" delete "care" and substitute --cap-- in its place.

In column 10, in claim 31, line 9, after "wherein said" delete "care" and substitute --cap-- in its place.

In column 10, in claim 31, line 10, after "when said" delete "care" and substitute --cap-- in its place.

In column 10, in claim 31, line 21, before "is in said second" delete "care" and substitute --cap-- in its place.

Signed and Sealed this

Twenty-fifth Day of November, 2008

JON W. DUDAS
*Director of the United States Patent and Trademark Office*